(12) United States Patent
Lee et al.

(10) Patent No.: US 9,662,032 B2
(45) Date of Patent: May 30, 2017

(54) BIOSIGNAL MEASURING APPARATUS AND METHOD OF MEASURING BIOSIGNAL

(71) Applicant: SAMSUNG ELECTRONICS CO., LTD., Suwon-si (KR)

(72) Inventors: Tak-hyung Lee, Seoul (KR); Byung-hoon Ko, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 342 days.

(21) Appl. No.: 13/626,125

(22) Filed: Sep. 25, 2012

(65) Prior Publication Data
US 2013/0079619 A1 Mar. 28, 2013

(30) Foreign Application Priority Data

Sep. 26, 2011 (KR) .................. 10-2011-0096990
Mar. 15, 2012 (KR) .................. 10-2012-0026790

(51) Int. Cl.
*A61B 5/0428* (2006.01)
*A61B 5/00* (2006.01)
*A61B 5/04* (2006.01)
*A61B 5/0408* (2006.01)

(52) U.S. Cl.
CPC ...... *A61B 5/04288* (2013.01); *A61B 5/04017* (2013.01); *A61B 5/04087* (2013.01); *A61B 5/7214* (2013.01)

(58) Field of Classification Search
CPC .............. A61B 5/7214; A61B 5/04288; A61B 5/04087; A61B 5/04017
USPC .................................. 600/393–397, 546–547
See application file for complete search history.

(56) References Cited

U.S. PATENT DOCUMENTS

| | | | | |
|---|---|---|---|---|
| 4,308,873 A | * | 1/1982 | Maynard | 600/544 |
| 4,793,361 A | | 12/1988 | DuFault | |
| 6,032,064 A | * | 2/2000 | Devlin et al. | 600/383 |
| 6,198,970 B1 | * | 3/2001 | Freed et al. | 607/42 |
| 6,208,888 B1 | | 3/2001 | Yonce | |
| 6,724,200 B2 | * | 4/2004 | Fukuda | 324/692 |

(Continued)

FOREIGN PATENT DOCUMENTS

DE      103 53 970 A1    7/2005
KR      10-0493714 B1    6/2005

(Continued)

OTHER PUBLICATIONS

European Search Report issued Apr. 26, 2013 in corresponding European Patent Application No. 12186030.8-1657/2572635.

(Continued)

*Primary Examiner* — Michael C Stout
(74) *Attorney, Agent, or Firm* — NSIP Law

(57) ABSTRACT

A biosignal measuring apparatus and a method of measuring a biosignal is provided. A biosignal measuring apparatus includes a first interfacing unit including two or more first interfaces configured to detect first signals from a subject, a second interfacing unit including two or more second interfaces and a connecting unit, the second interfaces being configured to detect noise from the subject, the connecting unit being configured to connect the second interfaces, and a biosignal extracting unit configured to extract a biosignal of the subject from the first signals by using signals output from the second interfacing unit.

12 Claims, 15 Drawing Sheets

(56) References Cited

U.S. PATENT DOCUMENTS

| | | |
|---|---|---|
| 6,912,414 B2 | 6/2005 | Tong |
| 7,623,916 B2* | 11/2009 | Julian .............................. 607/11 |
| 7,809,435 B1* | 10/2010 | Ettare et al. ................... 600/546 |
| 8,142,363 B1* | 3/2012 | Eigler et al. ................... 600/488 |
| 8,644,919 B2* | 2/2014 | Zdeblick ....................... 600/547 |
| 2003/0125635 A1* | 7/2003 | Maalouf et al. .............. 600/546 |
| 2003/0171661 A1* | 9/2003 | Tong .............................. 600/300 |
| 2005/0004490 A1* | 1/2005 | Organ et al. ................... 600/547 |
| 2005/0085741 A1* | 4/2005 | Hoskonen et al. ............ 600/544 |
| 2007/0270918 A1* | 11/2007 | De Bel et al. .................. 607/48 |
| 2008/0069375 A1* | 3/2008 | Lange .......................... 381/94.4 |
| 2008/0167701 A1* | 7/2008 | John et al. .................... 607/116 |
| 2008/0215128 A1* | 9/2008 | Rainey et al. ................. 607/152 |
| 2009/0124998 A1* | 5/2009 | Rioux et al. .................. 604/506 |
| 2009/0171233 A1* | 7/2009 | Lanfermann et al. ........ 600/546 |
| 2009/0283425 A1* | 11/2009 | Clark et al. ................... 205/792 |
| 2010/0022865 A1* | 1/2010 | Meyer ........................... 600/393 |
| 2010/0094081 A1* | 4/2010 | Rothe et al. .................. 600/104 |
| 2010/0152602 A1* | 6/2010 | Ross .............................. 600/544 |
| 2011/0028823 A1* | 2/2011 | Gilmore et al. .............. 600/391 |
| 2011/0037200 A1 | 2/2011 | McPherson |
| 2011/0046505 A1* | 2/2011 | Cornish et al. ............... 600/547 |
| 2011/0082383 A1* | 4/2011 | Cory et al. .................... 600/547 |
| 2011/0112605 A1* | 5/2011 | Fahey ............................. 607/48 |
| 2012/0190960 A1* | 7/2012 | Gilmore et al. .............. 600/393 |
| 2012/0245483 A1* | 9/2012 | Lundqvist ..................... 600/546 |

FOREIGN PATENT DOCUMENTS

| | | |
|---|---|---|
| KR | 10-0825888 B1 | 4/2008 |
| KR | 10-2009-0010947 A | 1/2009 |
| KR | 10-2010-0044384 A | 4/2010 |
| KR | 10-0964286 B1 | 6/2010 |
| KR | 10-2010-0104404 A | 9/2010 |
| KR | 10-2010-0107850 A | 10/2010 |
| KR | 10-1033472 B1 | 5/2011 |
| WO | WO 00/54650 | 9/2000 |
| WO | WO 2005/027720 A2 | 3/2005 |
| WO | WO 2007/063436 A1 | 6/2007 |
| WO | WO 2011/007292 A1 | 1/2011 |

OTHER PUBLICATIONS

Luo, Shen, and Willis J. Tompkins. "Experimental Study: Brachial Motion Artifact Reduction in the ECG." Computers in Cardiology IEEE, 1995 ( pp. 33-36 ).

* cited by examiner

BIOSIGNAL MEASURING APPARATUS AND METHOD OF MEASURING BIOSIGNAL

CROSS-REFERENCE TO RELATED APPLICATIONS

This application claims the benefit under 35 U.S.C. §119 (a) of Korean Patent Applications No. 10-2011-0096990, filed on Sep. 26, 2011, and No. 10-2012-0026790, filed on Mar. 15, 2012, in the Korean Intellectual Property Office, the entire disclosure of which is incorporated herein by reference for all purposes.

BACKGROUND

1. Field

The following description relates to a biosignal measuring apparatus and a method of measuring a biosignal.

2. Description of Related Art

The body is a type of conductor. As such, a small amount of current is generated in the body. As an example, a biosignal indicating inner characteristics of the body is measured using an electrode attached to the body to sense the small amount of current generated in the body or a change in the small amount of current generated in the body because of external stimuli.

SUMMARY

In one general aspect, a biosignal measuring apparatus includes a first interfacing unit including two or more first interfaces configured to detect first signals from a subject, a second interfacing unit including two or more second interfaces and a connecting unit, the second interfaces being configured to detect noise from the subject, the connecting unit being configured to connect the second interfaces, and a biosignal extracting unit configured to extract a biosignal of the subject from the first signals by using signals output from the second interfacing unit.

The apparatus may further include that the second interfaces include electrolytes, and the connecting unit includes an electrolyte configured to connect the electrolytes of the second interfaces.

The apparatus may further include that the electrolytes are hydrogels.

The apparatus may further include that the second interfaces include electrolytes, and the connecting unit includes a metal configured to connect the electrolytes of the second interfaces.

The apparatus may further include that the first interfacing unit and the second interfacing unit are attached to a pad.

The apparatus may further include that the first signals are outputted from the first interfacing unit, and the biosignal extracting unit is further configured to remove a result obtained from performing differential amplification on the outputted signals from the second interfacing unit from a result obtained from performing differential amplification on the outputted first signals to extract the biosignal from the first signals.

The apparatus may further include that the biosignal extracting unit includes a first differential amplifier, a second differential amplifier, an adaptive filter, and an adder, the first differential amplifier being configured to perform differential amplification on the outputted first signals, the second differential amplifier being configured to perform differential amplification on the outputted signals from the second interfacing unit, the adaptive filter being configured to adaptively filter a signal output from the second differential amplifier based on the extracted biosignal, the adder being configured to remove the adaptively filtered signal from a signal output from the first differential amplifier.

The apparatus may further include that, to extract the biosignal from the first signals, the biosignal extracting unit is further configured to remove a signal output from a twenty-first interface of the second interfaces from a signal output from an eleventh interface of the first interfaces, remove a signal output from a twenty-second interface of the second interfaces from a signal output from a twelfth interface of the first interfaces, and perform differential amplification on signals generated as a result of the removed signal of the twenty-first interface and the removed signal of the twenty-second interface.

The apparatus may further include that the biosignal extracting unit includes a first adaptive filter, a first adder, a second adaptive filter, a second adder, and a differential amplifier, the first adaptive filter being configured to adaptively filter the signal output from the twenty-first interface based on the extracted biosignal, the first adder being configured to remove an signal output from the first adaptive filter from the signal output from the eleventh interface, the second adaptive filter being configured to adaptively filter the signal output from the twenty-second interface based on the extracted biosignal, the second adder being configured to remove a signal output from the second adaptive filter from the signal output from the twelfth interface, the differential amplifier configured to perform differential amplification on a signal output from the first adder and a signal output from the second adder.

In another general aspect, a biosignal measuring apparatus includes a first interfacing unit including two or more first interfaces configured to detect first signals from a subject, a second interfacing unit including two or more second interfaces configured to detect noise from the subject, a distance between the second interfaces being less than a distance between the first interfaces, and a biosignal extracting unit configured to extract a biosignal of the subject from the first signals by using signals output from the second interfacing unit.

In yet another general aspect, a biosignal measuring apparatus includes an interfacing unit including two or more interfaces and a first switching device configured to switch a connection state between the interfaces, a control unit configured to control the first switching device to switch the connection state between the interfaces, and a biosignal extracting unit configured to remove signals output from the interfacing unit based on noise of a subject from signals output from the interfacing unit based on a biosignal of the subject to extract the noise from the biosignal, the signals being output from the interfacing unit according to the connection state of the controlled first switching device.

The apparatus may further include that the interfacing unit is configured to detect first signals when the control unit outputs a first control signal configured to open the first switching device.

The apparatus may further include that the interfacing unit is configured to detect noise signals when the control unit outputs a second control signal configured to short-circuit the first switching device.

The apparatus may further include that the detected first signals and the detected noise signals are outputted from the interfacing unit, the biosignal extracting unit includes a second switching device, the control unit is further configured to output a third control signal configured to control the second switching device, and, to extract the biosignal of the subject, the biosignal extracting unit is further configured to remove a result obtained from performing differential amplification on the outputted noise signals from a result obtained from performing differential amplification on the outputted first signals according to a switching result of the controlled second switching device.

The apparatus may further include that the biosignal extracting unit further includes a first differential amplifier, a second differential amplifier, an adaptive filter, and an adder, the first differential amplifier being configured to perform differential amplification on the outputted first signals, the second differential amplifier being configured to perform differential amplification on the outputted noise signals, the adaptive filter being configured to adaptively filter a signal output from the second differential amplifier based on the extracted biosignal, the adder being configured to remove the adaptively filtered signal from a signal output from the first differential amplifier.

The apparatus may further include that the detected first signals and the detected noise signals are outputted from the interfacing unit, the biosignal extracting unit includes a third switching device, the control unit is further configured to output a third control signal configured to control the third switching device, and, to extract the biosignal of the subject, the biosignal extracting unit is further configured to remove outputted noise signals from the outputted first signals according to a switching result of the controlled third switching device, and perform differential amplification on signals generated as a result of the removal of the outputted noise signals from the outputted first signals.

The apparatus may further include that the biosignal extracting unit further includes a first adaptive filter, a first adder, a second adaptive filter, a second adder, and a differential amplifier, the first adaptive filter being configured to adaptively filter a signal output from an eleventh interface of the interfaces based on the extracted biosignal as the first switching device is closed, the first adder being configured to remove a signal output from the first adaptive filter from a signal output from the eleventh interface as the first switching device is opened, the second adaptive filter being configured to adaptively filter a signal output from a twelfth interface of the interfaces based on the extracted biosignal as the first switching device is closed, the second adder being configured to remove a signal output from the second adaptive filter from a signal output from the twelfth interface as the first switching device is opened, the differential amplifier being configured to perform differential amplification on a signal output from the first adder and a signal output from the second adder.

In still another general aspect, there is provided a method of measuring a biosignal, the method including detecting first signals from a subject based on an eleventh interface and a twelfth interface, detecting noise from the subject based on a twenty-first interface and a twenty-second interface connected to the twenty-first interface, and extracting a biosignal of the subject from the first signals by using signals output from the twenty-first interface and the twenty-second interface based on the detected noise.

In a further general aspect, there is provided a method of measuring a biosignal, the method including outputting a first control signal, the first control signal being configured to control a switching device to have an open connection state between an eleventh interface and a twelfth interface, detecting first signals from of a subject according to the outputted first control signal, outputting a second control signal, the second control signal being configured to control the switching device to have a short-circuited connection state between the eleventh interface and the twelfth interface, detecting noise from the subject according to the outputted second control signal, and extracting a biosignal of the subject from the first signals by using the detected noise.

Other features and aspects may be apparent from the following detailed description, the drawings, and the claims.

Figure 1:
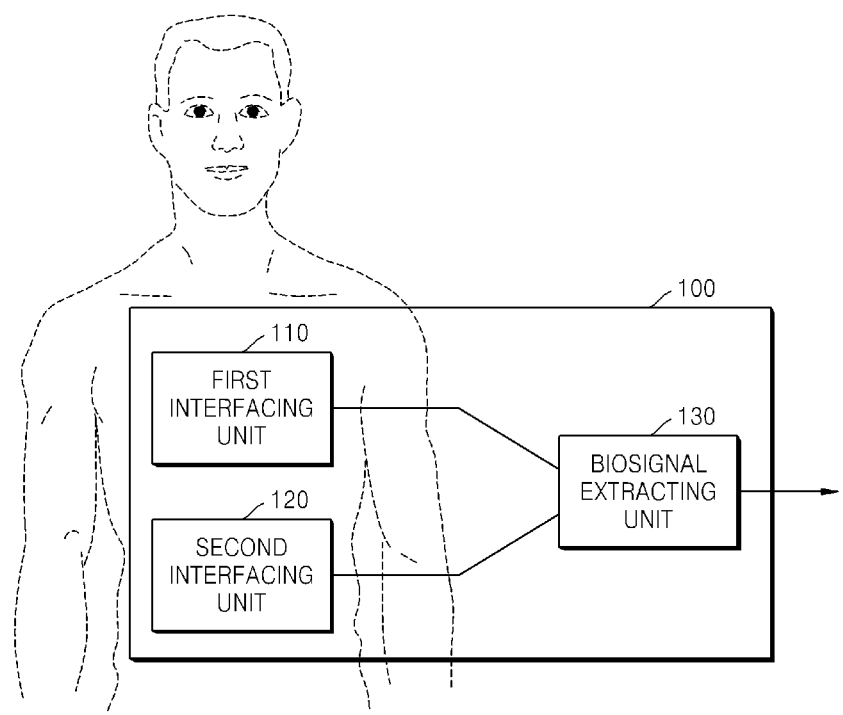
FIG. 1 is a block diagram illustrating an example of a biosignal measuring apparatus.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. In addition, descriptions of well-known functions and constructions may be omitted for increased clarity and conciseness.

FIG. 1 is a block diagram illustrating an example of a biosignal measuring apparatus 100. Referring to FIG. 1, the apparatus 100 includes a first interfacing unit 110, a second interfacing unit 120, and a biosignal extracting unit 130.

Examples of the biosignal measuring apparatus 100 include a medical apparatus and equipment configured to measure a biosignal of a subject. In an example, a biosignal is an electrical biosignal, and examples of the electrical biosignal include, but are not limited to, an electrocardiogram (ECG) signal, an electromyogram (EMG) signal, an electroencephalogram (EEG) signal, a galvanic skin resistance (GSR) signal, and an electro-oculogram (EOG) signal.

The first interfacing unit 110 includes at least two interfaces configured to detect a biosignal including noise from a subject. In an example, the biosignal including noise corresponds to a biosignal to which noise is added. In another example, the first interfacing unit 110 includes two interfaces configured to detect a signal and further includes an interface or a device known to one of ordinary skill in the art to be similar to an interface as a reference interface.

Each interface in FIG. 1 may be, but is not be limited to, an electrode configured to detect a signal from a subject by being placed in contact or close to the skin of the subject. In an example, the interface is a bioelectrode configured to measure a biosignal of a subject by applying a surface electrode attached to the skin of the subject. In this case, the electrode may include, but is not be limited to, a metal electrode, an electrolyte, and an adhesive sheet attached to the skin of the subject. A structure of the interface will be explained below with reference to FIG. 9.

In an example, the interface is classified into a wet-type electrode, a dry-type electrode, an insulating-type electrode, and a probe-type electrode. The wet-type electrode is interfaced with the skin of the subject via a gel-like material. The dry-type electrode is interfaced with the skin of the subject via a solid conductive material, such as a metal, a conductive fabric, or a conductive rubber. The insulating-type electrode is interfaced with the skin of the subject via capacitive coupling caused by an insulating material. In addition, the probe-type electrode is interfaced with the skin of the subject by penetrating through an outermost layer of the skin of the subject. As such, the insulating-type electrode is interfaced with the skin of the subject without contacting the skin of the subject because the insulating-type electrode uses capacitive coupling.

Accordingly, the at least two interfaces included in the first interfacing unit 110 are configured to detect a biosignal including noise from a subject, by contacting or being disposed close to the skin of the subject. The noise of the biosignal is generated resulting from a change in electrical characteristics of a signal transmission path. Examples of the noise include motion artifacts generated due to the motion of the subject, noise generated by the biosignal measuring apparatus 100, and noise generated resulting from a change in an axon action potential, an EMG, and respiration of the subject.

With respect to the motion artifacts, a half cell potential is generated in a double layer where different materials contact each other, between the metal electrode and the electrolyte included in the interface, and between the electrolyte of the interface and the skin of the subject. In this case, when a relative displacement occurs due to the motion of the subject, motion artifacts are generated resulting from the relative displacement. In an example in which a biosignal such as an ECG signal is measured, motion artifacts are distributed in a range from about 0.5 Hz to about 250 Hz, which is a frequency band similar to that of the ECG signal.

Accordingly, the first interfacing unit 110 detects a signal including noise from the subject. In an example, the detected signal including noise is a biosignal including noise.

The second interfacing unit 120 includes at least two interfaces configured to detect a noise signal and a connecting unit configured to connect the at least two interfaces. For example, the second interfacing unit 120 may include, but is not limited to, two interfaces configured to detect a noise signal, and may further include an interface used as a reference interface.

In an example, each interface included in the second interfacing unit 120 is an electrode configured to detect the noise signal from the subject by contacting or being disposed close to the skin of the subject. That is, in this example, the interface included in the second interfacing unit 120 is the same as the interface included in the first interfacing unit 110.

The connecting unit included in the second interfacing unit 120 connects the at least two interfaces included in the second interfacing unit 120 such that the interfaces are not electrically insulated from one another.

In an example, when the at least two interfaces are connected to each other by the connecting unit included in the second interfacing unit 120, since a biosignal of the subject is blocked in terms of circuit, the second interfacing unit 120 detects the reduced noise signal effect of the biosignal. Accordingly, in this example, the second interfacing unit 120 of FIG. 1 precisely detects the noise signal.

In another example, since a noise signal has a frequency band similar to that of a biosignal to be measured, it is difficult to remove noise by filtering. Accordingly, in this example, the biosignal measuring apparatus 100 of FIG. 1 uses the second interfacing unit 120 to accurately detect the noise signal.

The biosignal extracting unit 130 extracts a biosignal of the subject based on signals output from the first interfacing unit 110 and the second interfacing unit 120. In an example, the biosignal extracting unit 130 uses a differential amplifier to extract a biosignal based on hardware based calculation processing. In another example, the biosignal extracting unit 130 monitors and offsets the noise signal to extract a biosignal, which will be explained with reference to FIGS. 2A and 3A. However, the biosignal extracting unit 130 of FIG. 1 is not limited thereto. In yet another example, the biosignal extracting unit 130 of FIG. 1 monitors the noise signal and applies the noise signal to an adaptive filter (ADF) to extract a biosignal, which will be explained with reference to FIGS. 2B and 3B.

Accordingly, in an example, since the biosignal measuring apparatus 100 uses the second interfacing unit 120 to accurately detect the noise signal, a biosignal from which noise is removed is accurately detected. In addition, as noise is removed, the biosignal measuring apparatus 100 measures a biosignal with improved signal-to-noise ratio (SNR) characteristics. Furthermore, a biosignal including noise detected by the first interfacing unit 110 and a noise signal detected by the second interfacing unit 120 are detected at the same time from the same body part, thereby serving to effectively remove the noise signal from the biosignal including noise.

Figure 2A:
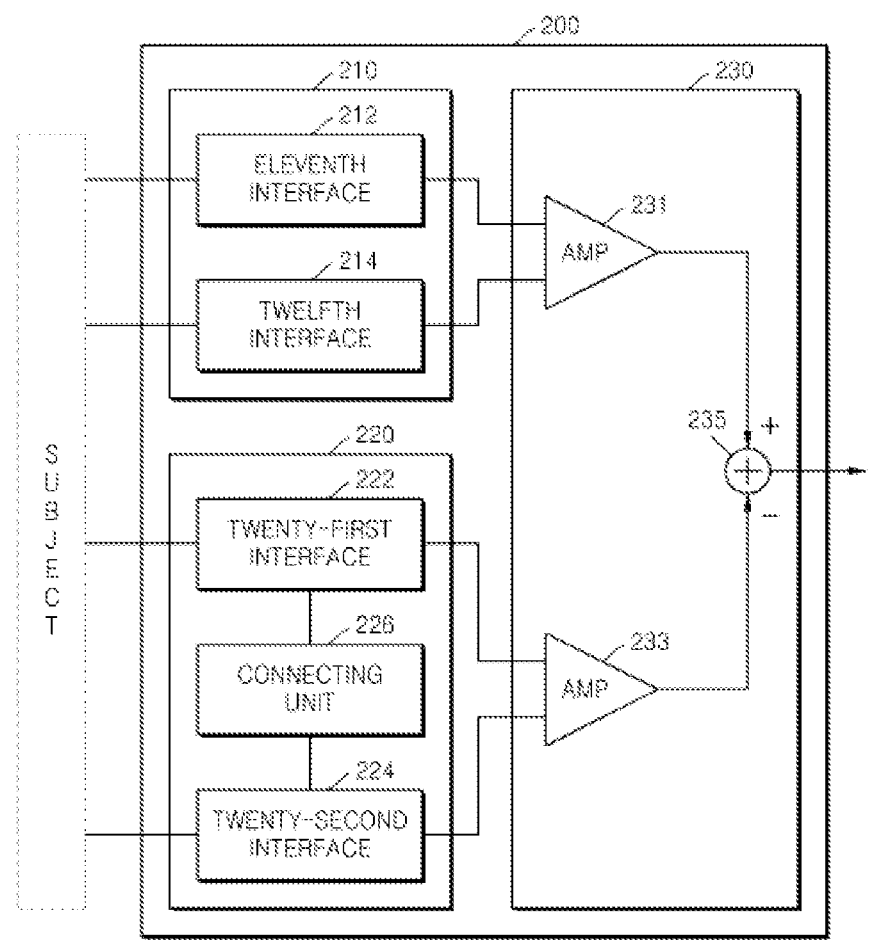
FIGS. 2A and 2B are block diagrams illustrating other examples of a biosignal measuring apparatus.

FIG. 2A is a block diagram illustrating an example of a biosignal measuring apparatus 200. Referring to FIG. 2A, the biosignal measuring apparatus 200 includes the first interfacing unit 210, the second interfacing unit 220, and the biosignal extracting unit 230. The first interfacing unit 210 includes an eleventh interface 212 and a twelfth interface 214. The second interfacing unit 220 includes a twenty-first interface 222, a twenty-second interface 224, and a connecting unit 226. The biosignal extracting unit 230 includes a first differential amplifier 231, a second differential amplifier 233, and an adder 235.

The biosignal measuring apparatus 200 of FIG. 2A is an example of the biosignal measuring apparatus 100 of FIG. 1. Accordingly, the biosignal measuring apparatus 200 of FIG. 2A is not limited to the units shown in FIG. 2A. In addition, the description with reference to FIG. 1 may apply to the biosignal measuring apparatus 200 of FIG. 2A, and, thus, a repeated explanation will not be given for corresponding elements.

The example illustrated in FIG. 2A is explained for convenience of explanation and not limited to a case where each of the first interfacing unit 210 and the second interfacing unit 220 includes two interfaces. Thus, in an example, each of the first interfacing unit 210 and the second interfacing unit 220 includes three or more interfaces.

The eleventh interface 212 and the twelfth interface 214 of the first interfacing unit 210 are configured to detect a biosignal including noise from a subject. The eleventh interface 212 and the twelfth interface 214 detect a biosignal including noise from a subject, and the biosignal including noise is transmitted to the biosignal extracting unit 230.

The second interfacing unit 220 includes the twenty-first interface 222, the twenty second interface 224, and the connecting unit 226 configured to connect the twenty-first interface 222 and the twenty-second interface 224. As shown in the example illustrated in FIG. 2A, the connecting unit 226 connects the twenty-first interface 222 and the twenty-second interface 224. For example, the connecting unit 226 short-circuits the twenty-first interface 222 and the twenty-second interface 224. Further, as a biosignal potential difference between ends of the connecting unit 226 decreases as a resistance of the connecting unit 226 decreases, a noise signal in a signal input to the biosignal extracting unit 230 is predominant. As a result, in an example, as the connecting unit 226 short-circuits the twenty-first interface 222 and the twenty-second interface 224, the second interfacing unit 220 detects the noise signal.

In an example, when the connecting unit 226 short-circuits the twenty-first and twenty-second interfaces 222 and 224, each of the twenty-first and twenty-second interfaces 222 and 224 includes an electrolyte. In a further example, the connecting unit 226 is an electrolyte configured to connect the electrolytes included in the twenty-first and twenty-second interfaces 222 and 224. In this case, each electrolyte may be, but is not limited to, a hydrogel, which is a conductive adhesive gel. Accordingly, in yet another example, since the twenty-first and twenty-second interfaces 222 and 224 are included in one hydrogel, the twenty-first and twenty-second interfaces 222 and 224 are electrically connected.

In an example, when the connecting unit 226 short-circuits the twenty-first and twenty-second interfaces 222 and 224, each of the twenty-first and twenty-second interfaces 222 and 224 includes an electrolyte. In a further example, the connecting unit 226 is a metal configured to connect the electrolytes included in the twenty-first and twenty-second interfaces 222 and 224. In this case, each electrolyte may be, but is not limited to, a hydrogel that is a conductive adhesive gel. Accordingly, in yet another example, as a metal is added to a hydrogel, a resistance of the connecting unit 226 configured to connect the twenty-first and twenty-second interfaces 222 and 224 is reduced. As such, in an example, the biosignal measuring apparatus 200 uses the second interfacing unit 220 to accurately extract the noise signal without using an additional sensor or similar device known to one of ordinary skill in the art.

As described above, the twenty-first interface 222 and the twenty-second interface 224 detect the noise signal and transmit the detected noise signal to the biosignal extracting unit 230. The biosignal extracting unit 230 uses signals output from the first interfacing unit 210 and the second interfacing unit 220 to extract a biosignal of the subject. In an example, the biosignal extracting unit 230 extracts a biosignal of the subject by removing a result obtained from performing differential amplification on signals output from the second interfacing unit 220 from a result obtained from performing differential amplification on signals output from the first interfacing unit 210.

For example, the first differential amplifier 231 performs differential amplification on a biosignal including noise output from the first interfacing unit 210. Further, the second differential amplifier 233 performs differential amplification on a noise signal output from the second interfacing unit 220. The adder 235 removes an output signal of the second differential amplifier 233 from an output signal of the first differential amplifier 231. In an example, the adder 235 removes the output signal of the second differential amplifier 233 in which a scale factor is considered from the output signal of the first differential amplifier 231. In this example, the scale factor is determined according to a result obtained from monitoring the noise signal, which will be explained with reference to FIG. 2B.

According to the example illustrated in FIG. 2A, the biosignal measuring apparatus 200 may accurately and efficiently extract a biosignal excluding noise of the subject, and the diagnosis accuracy using the extracted biosignal of the subject may be improved.

Figure 2B:
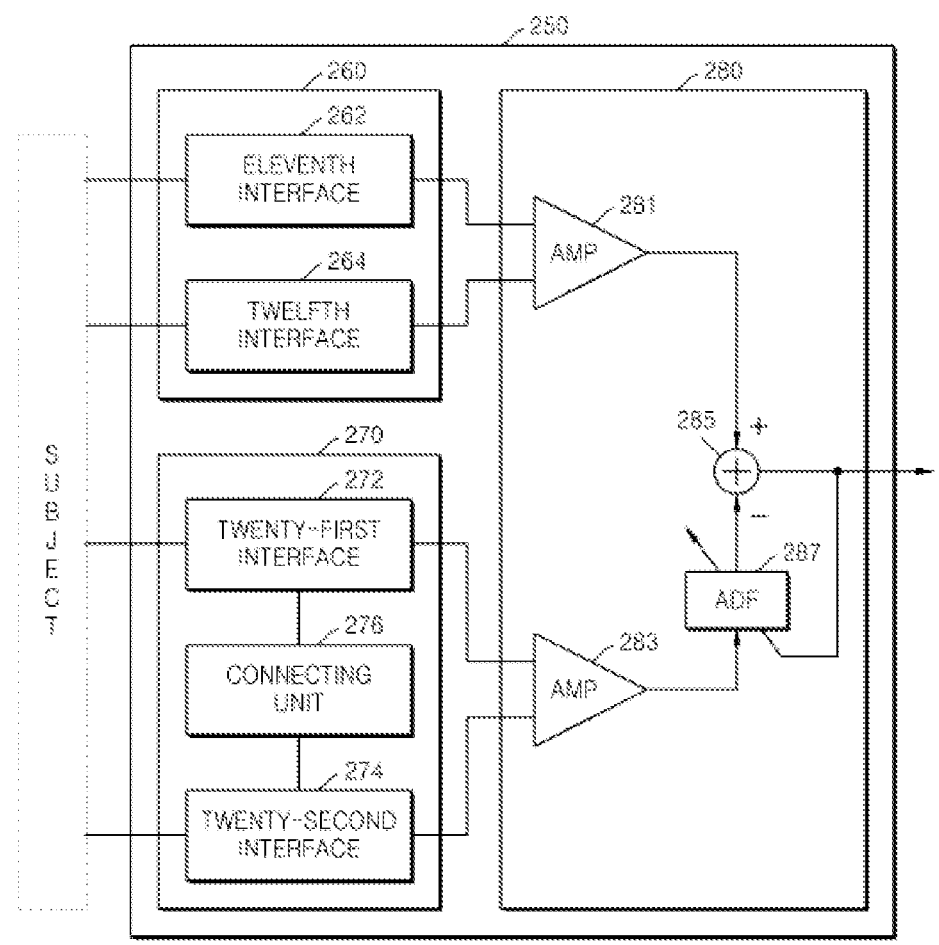

FIG. 2B is a block diagram illustrating another example of a biosignal measuring apparatus 250. Referring to the example illustrated in FIG. 2B, the biosignal measuring apparatus 250 includes a first interfacing unit 260, a second interfacing unit 270, and a biosignal extracting unit 280. The first interfacing unit 260 includes an eleventh interface 262 and a twelfth interface 264. The second interfacing unit 270 includes a twenty-first interface 272, a twenty-second interface 274, and a connecting unit 276. The biosignal extracting unit 280 includes a first differential amplifier 281, a second differential amplifier 283, an adder 285, and an ADF 287.

The apparatus 250 of FIG. 2B is an example of the apparatus 200 of FIG. 2A except that the ADF 287 is additionally included in the biosignal extracting unit 280, and thus a repeated explanation thereof will not be given for corresponding elements.

The ADF 287 adaptively filters a noise signal on which differential amplification is performed output from the second differential amplifier 283 based on a biosignal extracted by the adder 285.

For example, the ADF 287 updates a filter coefficient in order to converge a noise signal that is not completely removed from the biosignal extracted by the adder 285 to 0 (zero). In an example of this case, while not being limited thereto, the ADF 287 updates the filter coefficient in consideration of an artifact reduction percentage (ARP), a noise reduction ratio, and an SNR of the biosignal extracted by the adder 285.

The adder 285 removes an output signal of the ADF 287 from an output signal of the first differential amplifier 281. According to the example illustrated in FIG. 2B, the apparatus 250 of FIG. 2B may output a biosignal from which noise is completely removed by removing a noise signal by using a signal in which a scale factor is considered while passing through the ADF 287.

Figure 3A:
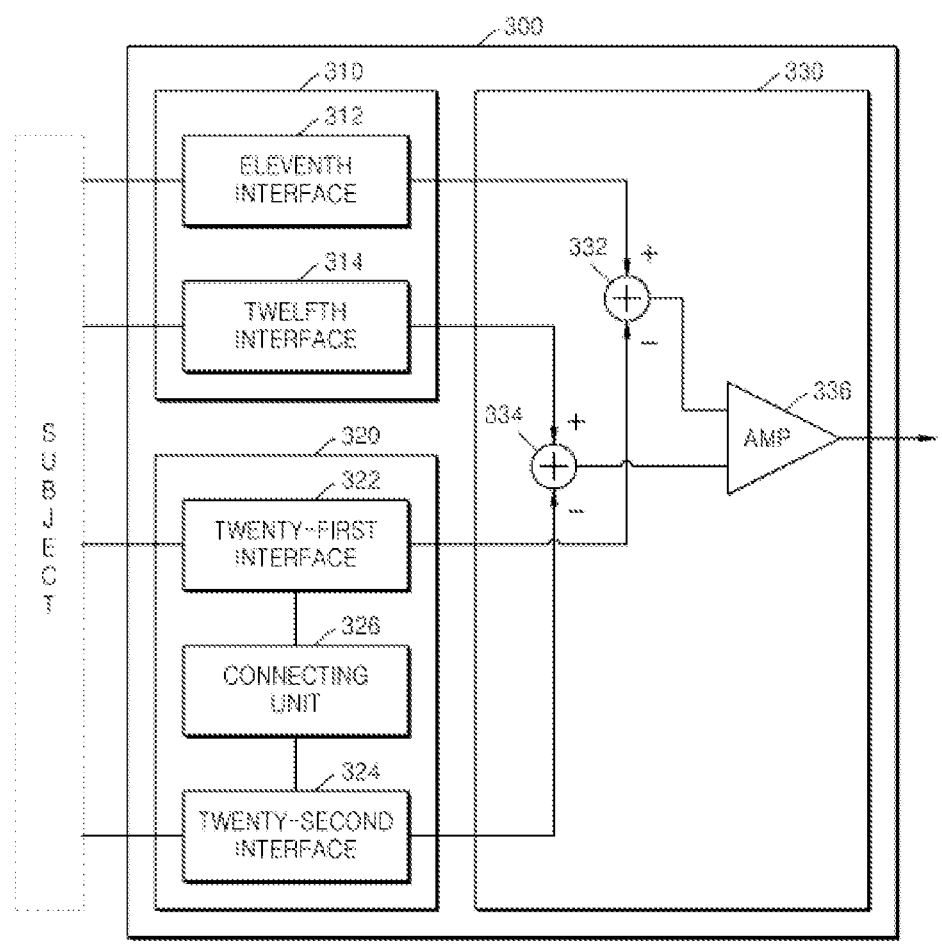
FIGS. 3A and 3B are block diagrams illustrating further examples of a biosignal measuring apparatus.

FIG. 3A is a block diagram illustrating another example of a biosignal measuring apparatus 300. Referring to the example illustrated in FIG. 3A, the apparatus 300 includes a first interfacing unit 310, a second interfacing unit 320, and a biosignal extracting unit 330. The first interfacing unit 310 includes an eleventh interface 312 and a twelfth interface 314. The second interfacing unit 320 includes a twenty-first interface 322, a twenty-second interface 324, and a connecting unit 326. The biosignal extracting unit 330 includes a first adder 332, a second adder 334, and a differential amplifier 336.

The apparatus 300 of FIG. 3A is an example of the apparatus 100 of FIG. 1. Accordingly, the apparatus 300 of FIG. 3A is not limited to the units shown in FIG. 3A. In addition, a description made with reference to FIG. 1 may apply to the apparatus 300 of FIG. 3A, and a repeated explanation will not be given with respect to corresponding elements. Further, the apparatus 300 of FIG. 3 is an example of the apparatus 200 of FIG. 2A except for a structure of the biosignal extracting unit 330, and thus, a repeated explanation will not be given with respect to corresponding elements thereof.

The first interfacing unit 310 detects a biosignal including noise and transmits the biosignal to the biosignal extracting unit 330. The second interfacing unit 320 detects a noise signal and transmits the noise signal to the biosignal extracting unit 330.

The biosignal extracting unit 330 extracts a biosignal of a subject by using signals output from the first interfacing unit 310 and the second interfacing unit 320. For example, the biosignal extracting unit 330 extracts a biosignal of a subject by removing an output signal of the twenty-first interface 322 from an output signal of the eleventh interface 112, removing an output signal of the twenty-second interface 324 from an output signal of the twelfth interface 114, and performing differential amplification on signals generated due to the removal.

For example, the first adder 332 removes an output signal of the twenty-first interface 322 from an output signal of the eleventh interface 312, the second adder 334 removes an output signal of the twenty-second interface 324 from an output signal of the twelfth interface 314, and the differential amplifier 336 performs differential amplification on signals generated due to the removal. In an example of this case, the first adder 332 removes an output signal of the twenty-first interface 322 in which a scale factor is considered from an output signal of the eleventh interface 312, and the second adder 334 removes an output signal of the twenty-second interface 324 in which a scale factor is considered from an output signal of the twelfth interface 314. In another example of this case, the scale factor is determined according to a result obtained from monitoring the noise signal, which will be explained with reference to FIG. 3B.

Accordingly, the apparatus 300 of FIG. 3A may accurately and efficiently extract a biosignal excluding noise of the subject, by using the differential amplifier 336, and the diagnosis accuracy using the extracted biosignal of the subject may be improved.

Figure 3B:
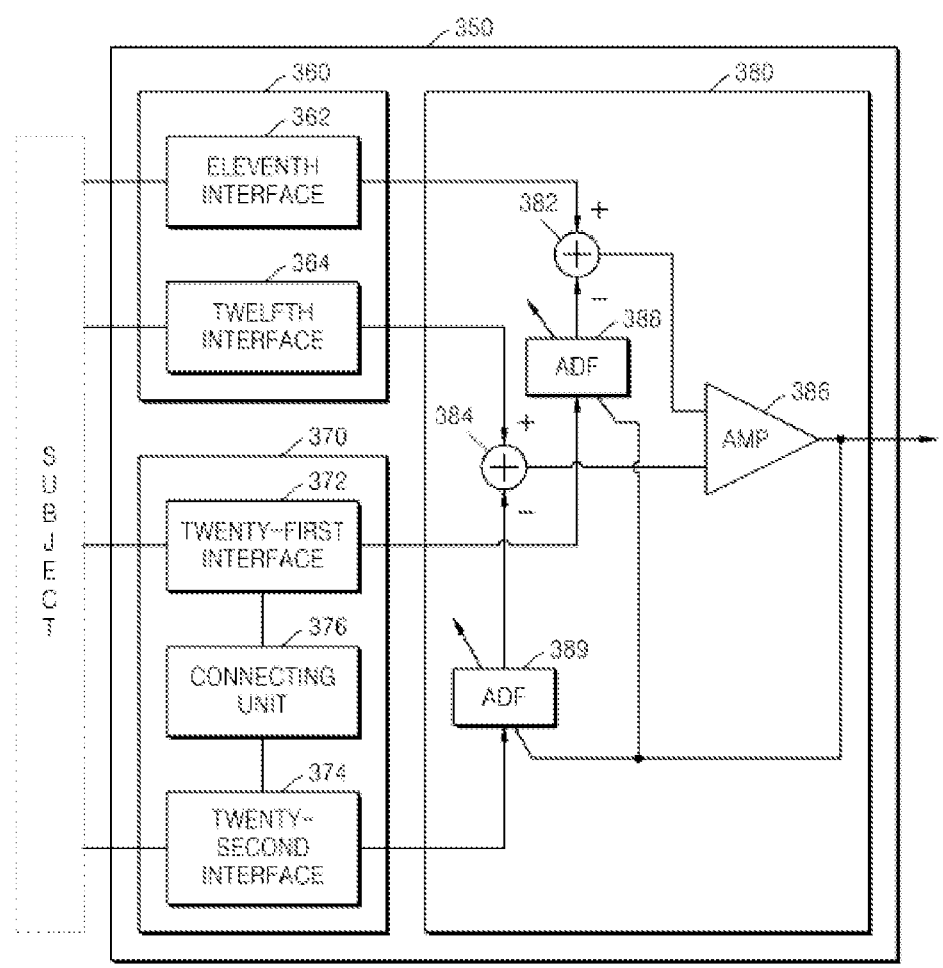

FIG. 3B is a block diagram illustrating another example of a biosignal measuring apparatus 350. Referring to the example illustrated in FIG. 3B, the biosignal measuring apparatus 350 includes a first interfacing unit 360, a second interfacing unit 370, and a biosignal extracting unit 380. The first interfacing unit 360 includes an eleventh interface 362 and a twelfth interface 364. The second interfacing unit 370 includes a twenty-first interface 372, a twenty-second interface 374, and a connecting unit 376. The biosignal extracting unit 380 includes a first adder 382, a second adder 384, a differential amplifier 386, a first ADF 388, and a second ADF 389.

The apparatus 350 of FIG. 3B is an example of the apparatus 300 of FIG. 3A except that the first ADF 388 and the second ADF 389 are additionally included in the biosignal extracting unit 380, and thus a repeated explanation thereof will not be given with respect to corresponding elements.

The first ADF 388 adaptively filters an output signal of the twenty-first interface 372 based on a biosignal output from the third differential amplifier 386, and the second ADF 389 adaptively filters an output signal of the twenty-second interface 374 based on the biosignal output from the differential amplifier 386.

For example, the first ADF 388 and the second ADF 389 update a filter coefficient in order to converge a noise signal that is not completely removed from the biosignal output from the differential amplifier 386 to 0 (zero). In an example of this case, while not being limited thereto, the first ADF 388 and the second ADF 389 updates a filter coefficient in consideration of an artifact reduction percentage (ARP), a noise reduction ratio, and an SNR of the biosignal output from the differential amplifier 386.

The first adder 382 removes an output signal of the first ADF 388 from an output signal of the eleventh interface 362. The second adder 384 removes an output signal of the second ADF 389 from an output signal of the twelfth interface 364. The differential amplifier 386 performs differential amplification on signals generated due to the removal.

Accordingly, the apparatus 350 of FIG. 3B may output a biosignal from which noise is completely removed by removing a noise signal by using a signal in which a scale factor is considered while passing through the first ADF 388 and the second ADF 389.

Figure 4:
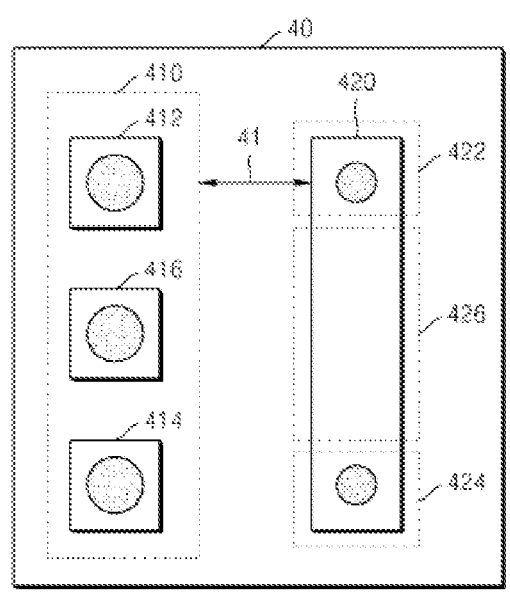
FIG. 4 is a block diagram illustrating an example of a first interfacing unit and a second interfacing unit of a biosignal measuring apparatus.

FIG. 4 is a block diagram illustrating an example of a first interfacing unit 410 and a second interfacing unit 420 of a biosignal measuring apparatus. Referring to the example illustrated in FIG. 4, the first interfacing unit 410 and the second interfacing unit 420 are attached to a pad 40. As an example of such, the first interfacing unit 410 and the second interfacing unit 420 attached to the pad 40 are realized as a hybrid electrode.

The first interfacing unit 410 includes the eleventh interface 412 and the twelfth interface 414, which are configured to measure a biosignal including noise from a subject. In addition, while not being limited thereto, the first interfacing unit 410 further includes a thirteenth interface 416 as a reference interface.

The second interfacing unit 420 includes the twenty-first interface 422, the twenty-second interface 424, and the connecting unit 426. In an example of this case, while not being limited thereto, the twenty-first interface 422 and the twenty-second interface 424 share the thirteenth interface 416 as a reference interface.

In an example, the connecting unit 426 short-circuits the twenty-first interface 422 and the twenty-second interface 424. That is, in this example, the connecting unit 426 is an electrolyte configured to connect electrolytes included in the twenty-first interface 422 and the twenty-second interface 424, or a metal configured to connect electrolytes included in the twenty-first interface 422 and the twenty-second interface 424.

In addition, in another example, a distance 41 between the first interfacing unit 410 and the second interfacing unit 420 is less than about 5 cm. In an alternative example, as the first interfacing unit 410 and the second interfacing unit 420 are located on the pad 40, the first interfacing unit 410 and the second interfacing unit 420 is attached to the same body part of the subject. As such, as a signal is measured when the first interfacing unit 410 and the second interfacing unit 420 are disposed close to each other, the accuracy of measuring a biosignal from the subject may be improved.

As the example of the first interfacing unit 410 and the second interfacing unit 420 is realized as illustrated in FIG. 4, a biosignal of a subject may be accurately and conveniently measured.

Figure 5:
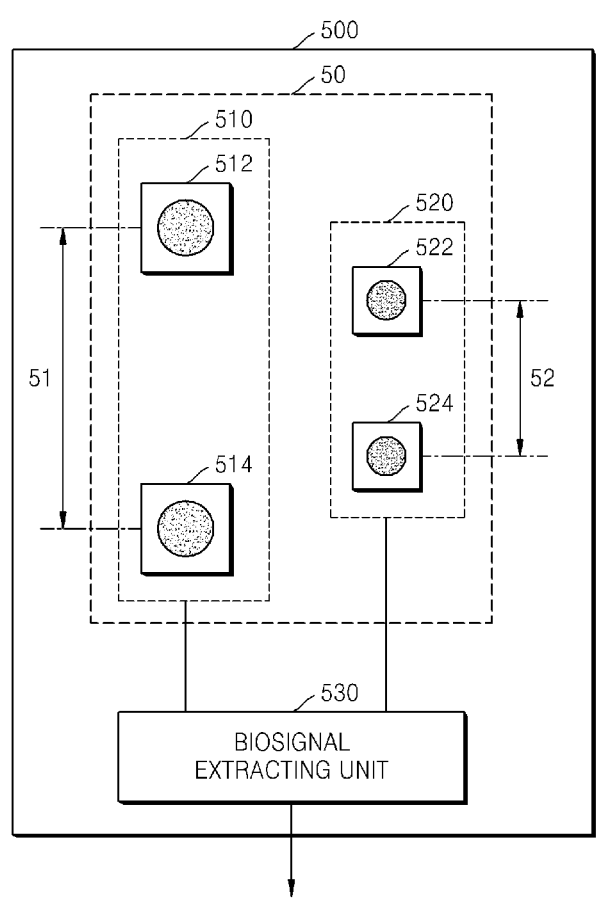
FIG. 5 is a block diagram illustrating another example of a biosignal measuring apparatus.

FIG. 5 is a block diagram illustrating another example of a biosignal measuring apparatus 500. Referring to FIG. 5, the apparatus 500 includes a first interfacing unit 510, a second interfacing unit 520, and a biosignal extracting unit 530. The first interfacing unit 514 includes an eleventh interface 512 and a twelfth interface 514, and the second interfacing unit 520 includes a twenty-first interface 522 and a twenty-second interface 524.

The apparatus 500 of FIG. 5 is another example of the apparatus 100 of FIG. 1. Accordingly, the apparatus 500 of FIG. 5 is not limited to the units shown in FIG. 5. Further, the description of FIG. 1 may apply to the apparatus 500 of FIG. 5, and thus, a repeated explanation will not be given with respect to corresponding elements.

In addition, the apparatus 500 of FIG. 5 is another example of the apparatuses 200, 250, 300, and 350 of FIGS. 2A-3B and the example of the first and second interfacing units 410 and 420 illustrated in FIG. 4 except that the second interfacing unit 520 does not include the connecting unit 226, 276, 326, 376, and 426, and thus, a repeated explanation will not be given with respect to corresponding elements.

The first interfacing unit 510 includes the eleventh interface 512 and the twelfth interface 514 that are configured to detect a biosignal including noise from a subject. The second interfacing unit 520 includes the twenty-first interface 522 and the twenty-second interface 524 configured to detect a noise signal. In an example of this case, a distance 52 between the twenty-first interface 522 and the twenty-second interface 524 included in the second interfacing unit 520 is less than a distance 51 between the eleventh interface 512 and the twelfth interface 514 included in the first interfacing unit 510. In accordance with the example illustrated in FIG. 5, the second interfacing unit 520 may detect the reduced noise signal effect of the biosignal.

The biosignal extracting unit 530 extracts a biosignal of the subject by using signals output from the first interfacing unit 510 and the second interfacing unit 520. In accordance with the example illustrated in FIG. 5, the biosignal measuring apparatus 500 may use the second interfacing unit 520 to measure a biosignal of the subject with improved SNR characteristics.

Figure 6:
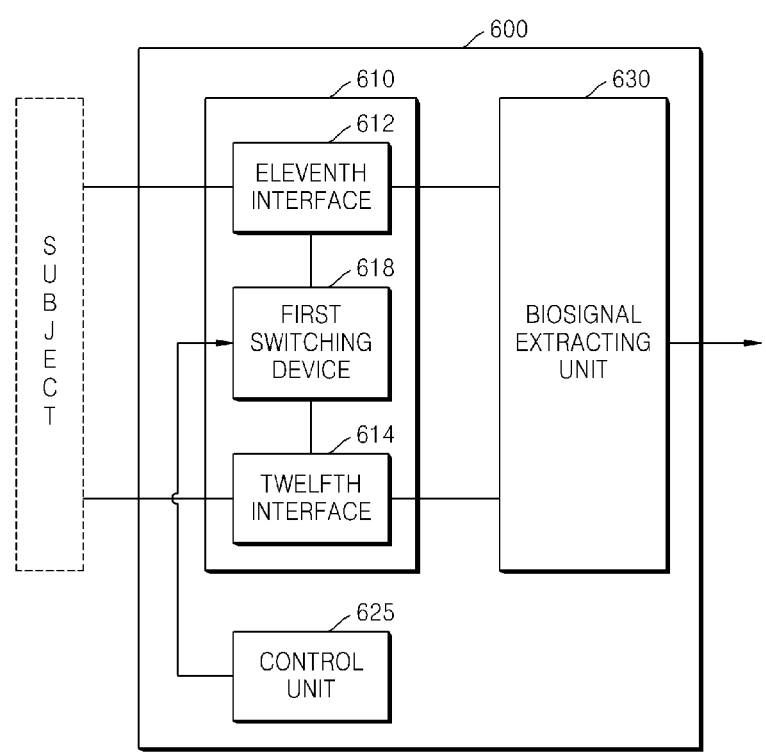
FIG. 6 is a block diagram illustrating yet another example of a biosignal measuring apparatus.

FIG. 6 is a block diagram illustrating another example of a biosignal measuring apparatus 600. Referring to the example illustrated in FIG. 6, the apparatus 600 includes an interfacing unit 610, a control unit 625, and a biosignal extracting unit 630. The interfacing unit 610 includes an eleventh interface 612, a twelfth interface 614, and a first switching device 618.

The apparatus 600 of FIG. 6 is another example of the apparatus 100 of FIG. 1. Accordingly, the apparatus 600 of FIG. 6 is not limited to the units shown in FIG. 6. In addition, the description with reference to FIG. 1 may apply to the apparatus 600 of FIG. 6, and thus, a repeated explanation will not be given with respect to corresponding elements.

Further, the apparatus 600 of FIG. 6 is the same as the realized embodiment of the apparatus 200, 250, 300, 350 of FIGS. 2A-3B and the first and second interfacing units 410 and 420 of FIG. 4 except that the apparatus 600 does not include the second interfacing unit 220, 270, 320, 370, and 420, and thus, a repeated explanation will not be given with respect to corresponding element.

The interfacing unit 610 includes at least two interfaces and the first switching device 618 configured to switch a connection state between the at least two interfaces. For example, the interfacing unit 610 includes the eleventh interface 612 and the twelfth interface 614 configured to detect a biosignal including noise, a noise signal, or a combination thereof. In addition, the interfacing unit 610 includes the first switching device 618 configured to switch a connection state between the eleventh interface 612 and the twelfth interface 614. In an example of this case, while not being limited thereto, the first switching device 618 includes a switch, a transistor, a metal-oxide-semiconductor field-effect transistor (MOSFET), a relay, and other elements known to one of ordinary skill in the art to be included in switching devices, and additionally includes any device configured to perform a switching operation under the control of the control unit 625.

The control unit 625 controls the first switching device 618 included in the interfacing unit 610. According to an example, while not being limited thereto, the control unit 625 outputs a control signal and a clock signal configured to control the first switching device 618.

For example, the control unit 625 outputs a control signal configured to open the first switching device 618, and detects a biosignal including noise by using the interfacing unit 610. Alternatively, the control unit 625 outputs a control signal configured to close the first switching device 618, and detects a noise signal by using the interfacing unit 610. In accordance with the example illustrated in FIG. 6, the interfacing unit 610 may selectively output a biosignal including noise or a noise signal under the control of the control unit 625.

The biosignal extracting unit 630 extracts a biosignal of a subject by using signals output according to a connection state between the at least two interfaces included in the interfacing unit 610 under the control of the control unit 625. For example, the biosignal extracting unit 630 receives a biosignal including noise from the eleventh interface 612 and the twelfth interface 614 when the first switching device 618 is opened under the control of the control unit 625, and receives a noise signal from the eleventh interface 612 and the twelfth interface 614 when the first switching device 618 is closed under the control of the control unit 625.

In accordance with the example illustrated in FIG. 6, the biosignal extracting unit 630 extracts a biosignal of a subject by using the biosignal to which the noise is added and the noise signal, which will be explained with reference to FIGS. 7A through 8B. Further, the apparatus 600 of FIG. 6 may measure a biosignal of a subject with improved SNR characteristics without using an additional interface.

Figure 7A:
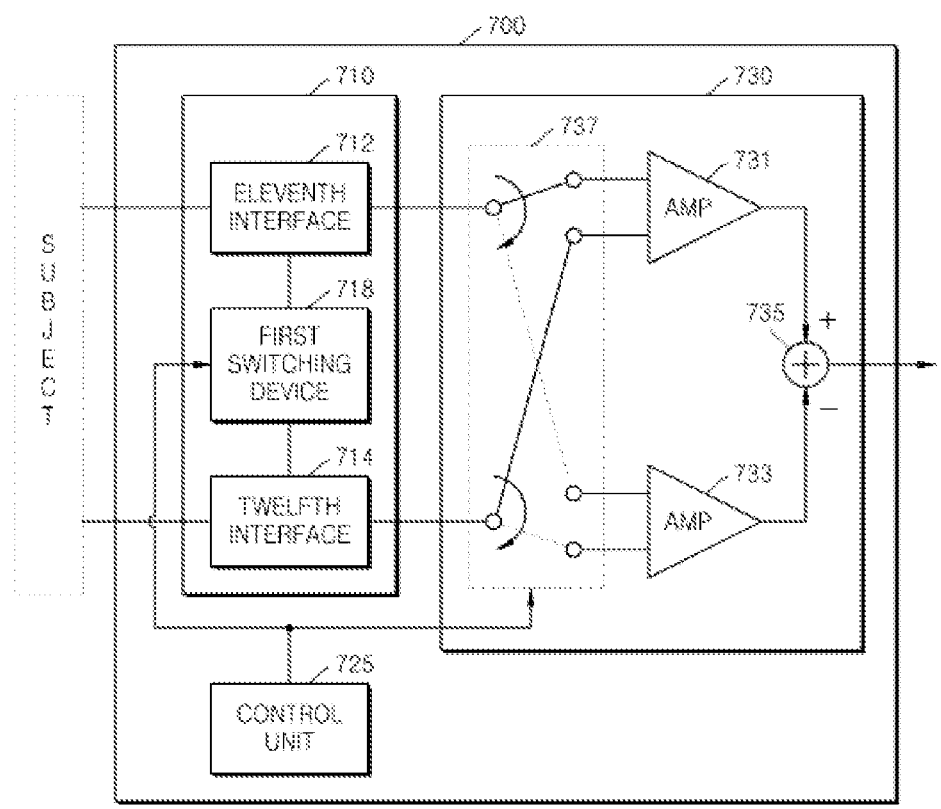
FIGS. 7A and 7B are block diagrams illustrating other examples of a biosignal measuring apparatus.

FIG. 7A is a block diagram illustrating another example of a biosignal measuring apparatus 700. Referring to the example illustrated in FIG. 7A, the apparatus 700 includes an interfacing unit 710, a control unit 725, and a biosignal extracting unit 730. The interfacing unit 710 includes a eleventh interface 712, a twelfth interface 714, and a first switching device 718 configured to switch a connection state between the eleventh and twelfth interfaces 712 and 714. The biosignal extracting unit 730 includes a first differential amplifier 731, a second differential amplifier 733, an adder 735, and a second switching device 737.

The apparatus 700 of FIG. 7A is another example of the apparatus 600 of FIG. 6. Accordingly, the apparatus 700 of FIG. 7A is not limited to units shown in FIG. 7A. In addition, a description made with reference to FIG. 6 may apply to the apparatus 700 of FIG. 7A, and a repeated explanation will not be given with respect to corresponding elements.

The control unit 725 controls the first switching device 718 included in the interfacing unit 710 and the second switching device 737 included in the biosignal extracting unit 730. For example, the control unit 725 outputs a control signal configured to open the first switching device 718, and detects a biosignal including noise by using the interfacing unit 710. Alternatively, the control unit 725 outputs a control signal configured to close the first switching device 718, and detects a noise signal by using the interfacing unit 710. In addition, in an example, the control unit 725 further outputs a control signal configured to control the second switching device 737.

The biosignal extracting unit 730 extracts a biosignal of a subject by using signals output according to a connection state between the eleventh interface 712 and the twelfth interface 714 under the control of the control unit 725. For example, the control unit 725 outputs a control signal configured to control the second switching device 737, and the biosignal extracting unit 730 extracts a biosignal of a subject by removing a result obtained from performing differential amplification on a noise signal from a result obtained from performing differential amplification on a biosignal including noise according to a switching result of the second switching device 737.

For example, as a control signal configured to open the first switching device 718 is output from the control unit 725 to insulate the eleventh interface 712 and the twelfth interface 714, the control unit 725 outputs a control signal configured to control the second switching device 737. Based on a switching result of the second switching device 737 under the control of the control unit 725, the biosignal extracting unit 730 transmits a biosignal including noise output from the interfacing unit 710 to the first differential amplifier 731.

In addition, as a control signal configured to close the first switching device 718 is output from the control unit 725 to short-circuit the eleventh interface 712 and the twelfth interface 714, the control unit 725 outputs a control signal configured to control the second switching device 737. Based on a switching result of the second switching device 737 under the control of the control unit 725, the biosignal extracting unit 630 transmits a noise signal output from the interfacing unit 710 to the second differential amplifier 733.

The adder 735 extracts a biosignal of a subject by removing a result obtained from performing differential amplification by using the second differential amplifier 733 from a result obtained from performing differential amplification by using the first differential amplifier 731. For example, the first differential amplifier 731 performs differential amplification on a biosignal including noise, the second differential amplifier 733 performs differential amplification on a noise signal, and the adder 735 removes an output signal of the second differential amplifier 733 from an output signal of the first differential amplifier 731. In an example of this case, the adder 735 removes an output signal of the second differential amplifier 733 in which a scale factor is considered from an output signal of the first differential amplifier 731. In another example of this case, the scale factor is determined according to a result obtained from monitoring the noise signal, which will be explained with reference to FIG. 7B.

In accordance with the example illustrated in FIG. 7A, the apparatus 700 may accurately and efficiently extract a biosignal of a subject from which noise is removed, and diagnosis accuracy using the extracted biosignal of the subject may be improved.

Figure 7B:
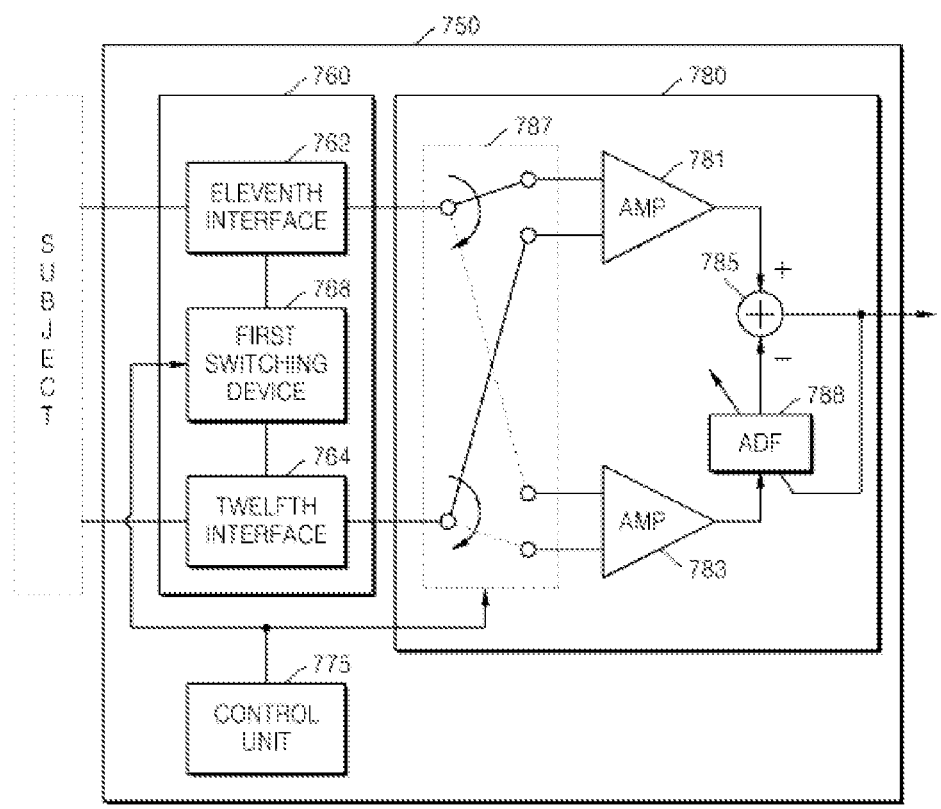

FIG. 7B is a block diagram illustrating another example of a biosignal measuring apparatus 750. Referring to the example illustrated in FIG. 7B, the apparatus 750 includes an interfacing unit 760, a control unit 775, and a biosignal extracting unit 780. The interfacing unit 760 includes an eleventh interface 762, a twelfth interface 764, and a first switching device 768. The biosignal extracting unit 780 includes a first differential amplifier 781, a second differential amplifier 783, an adder 785, a second switching device 787, and an ADF 788.

The apparatus 750 of FIG. 7B is another example of the apparatus 700 of FIG. 7A except that the ADF 788 is additionally included in the biosignal extracting unit 780, and thus a repeated explanation thereof will not be given with respect to corresponding elements.

The ADF 788 adaptively filters a noise signal on which differential amplification is performed output from the second differential amplifier 783 based on a biosignal extracted by the adder 785. The ADF 788 of FIG. 7B is another example of the ADF 287 of FIG. 2B, and thus a repeated explanation thereof will not be given with respect to corresponding elements.

Figure 8A:
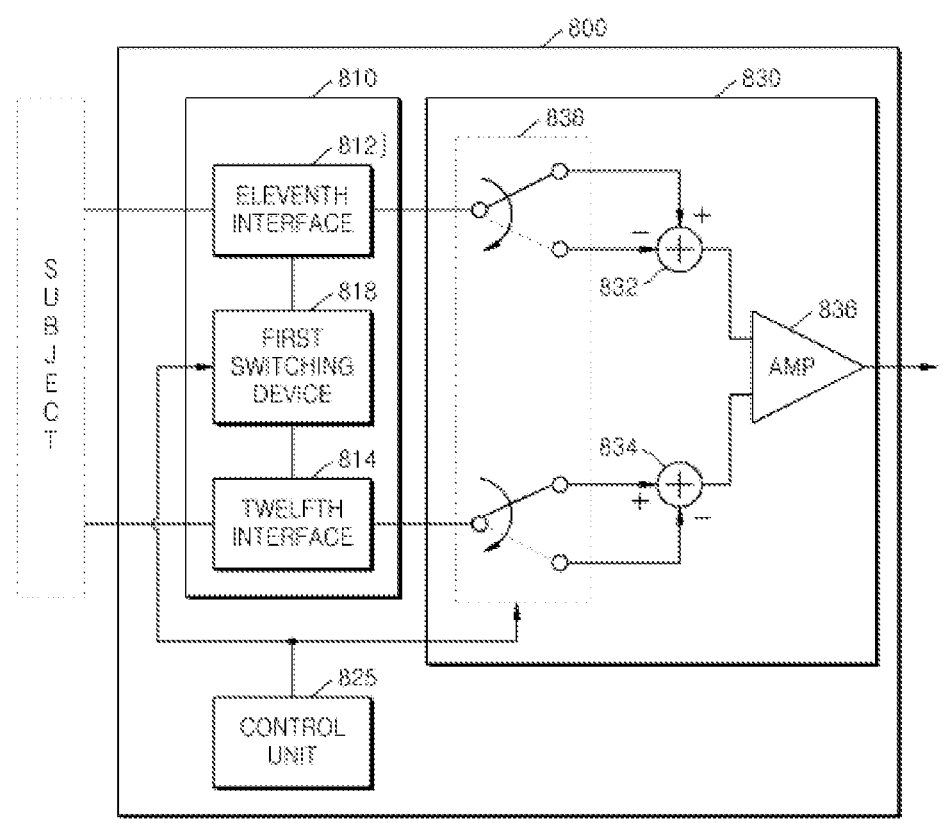
FIGS. 8A and 8B are block diagrams illustrating further example of a biosignal measuring apparatus.

FIG. 8A is a block diagram illustrating another example of a biosignal measuring apparatus 800. Referring to the example illustrated in FIG. 8A, the apparatus 800 includes an interfacing unit 810, a control unit 825, and a biosignal extracting unit 830. The interfacing unit 810 includes an eleventh interface 812, a twelfth interface 814, and a first switching device 818 configured to switch a connection state between the eleventh and twelfth interfaces 812 and 814. The biosignal extracting unit 830 includes a first adder 832, a second adder 834, a differential amplifier 836, and a second switching device 838.

The apparatus 800 of FIG. 8A is another example of the apparatus 600 of FIG. 6. Accordingly, the apparatus 800 of FIG. 8A is not limited to the units shown in FIG. 8A. In addition, the description with reference to FIG. 6 may apply to the apparatus 800 of FIG. 8A, and thus, a repeated explanation will not be given with respect to corresponding elements.

Further, the apparatus 800 of FIG. 8A is another example of the apparatus 700 of FIG. 7A except for a structure of the biosignal extracting unit 830, and thus, a repeated explanation will not be given with respect to corresponding elements.

The control unit 825 controls the first switching device 818 included in the interfacing unit 810, and the second switching device 838 included in the biosignal extracting unit 830. The biosignal extracting unit 830 extracts a biosignal of a subject by using signals output according to a connection state between the eleventh interface 812 and the twelfth interface 814 under the control of the control unit 825. For example, the control unit 825 outputs a control signal configured to control the second switching device 838, and the biosignal extracting unit 830 extracts a biosignal of a subject by removing a noise signal from a biosignal including noise according to a switching result of the second switching device 838 and performing differential amplification on signals generated due to the removal.

For example, as a control signal configured to open the first switching device 818 is output from the control unit 825 to insulate the eleventh interface 812 and the twelfth interface 814, the control unit 825 outputs a control signal configured to control the second switching device 838.

According to a switching result of the third switching device 838 under the control of the control unit 825, the biosignal extracting unit 830 transmits a biosignal that includes noise and is output from the interfacing unit 810 to positive (+) terminals of the first adder 832 and the second adder 834.

In addition, as a control signal configured to close the first switching device 818 is output from the control unit 825 to short-circuit the eleventh interface 812 and the twelfth interface 814, the control unit 825 outputs a control signal configured to control the second switching device 838. According to a switching result of the second switching device 838 under the control of the control unit 825, the biosignal extracting unit 830 transmits a noise signal output from the interfacing unit 810 to negative (−) terminals of the first adder 832 and the second adder 834.

The first adder 832 and the second adder 834 remove a noise signal from a biosignal including noise. The differential amplifier 836 performs differential amplification on signals generated due to the removal. In an example of this case, the first adder 832 and the second adder 834 remove a noise signal in which a scale factor is considered from a biosignal including noise. In another example of this case, the scale factor is determined according to a result obtained from monitoring the noise signal, which will be explained with reference to FIG. 8B.

According to the example illustrated in FIG. 8A, the apparatus 800 may accurately and efficiently extract a biosignal excluding noise of a subject by using the differential amplifier 836, and the diagnosis accuracy using the extracted biosignal of the subject may be improved.

Figure 8B:
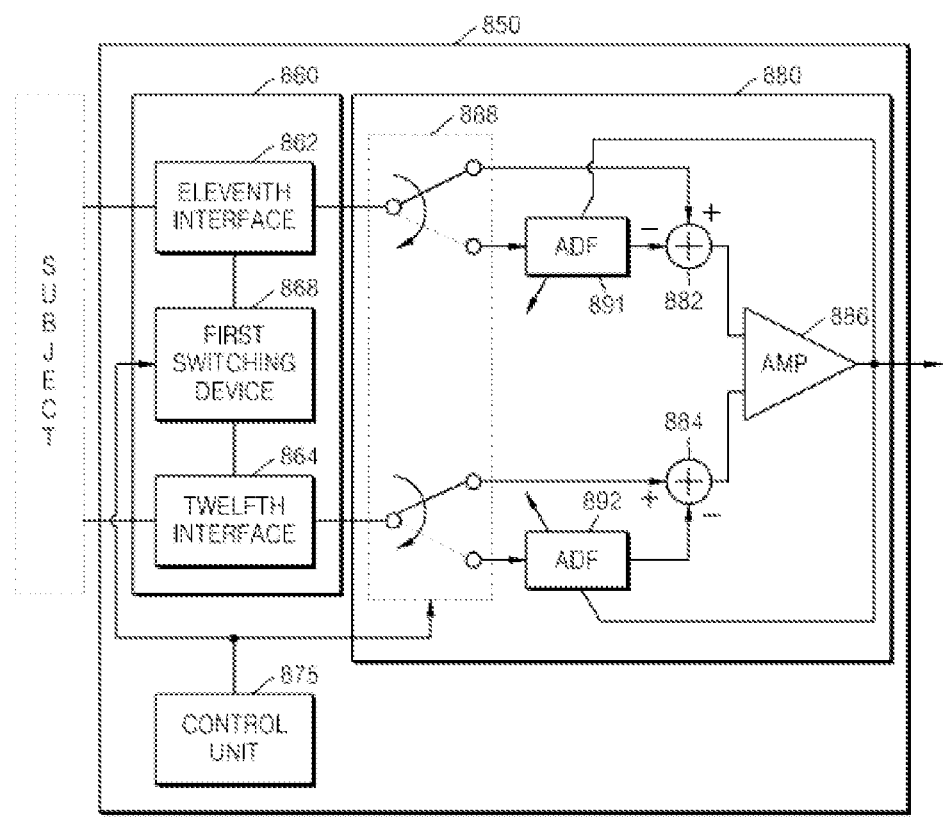

FIG. 8B is a block diagram illustrating another example of a biosignal measuring apparatus 850. Referring to the example illustrated in FIG. 8B, the apparatus 850 includes an interfacing unit 860, a control unit 875, and a biosignal extracting unit 880. The interfacing unit 860 includes an eleventh interface 862, a twelfth interface 864, and a first switching device 868. The biosignal extracting unit 880 includes a first adder 882, a second adder 884, a differential amplifier 886, a second switching device 888, a first ADF 891, and a second ADF 892.

The apparatus 850 of FIG. 8B is another example of the apparatus 800 of FIG. 8A except that the first ADF 891 and the second ADF 892 are additionally included in the biosignal extracting unit 880, and thus a repeated explanation thereof will not be given with respect to corresponding elements.

As a control signal configured to close the first switching device 868 and a control signal configured to control the second switching device 888 are output from the control unit 875, a noise signal output from the interfacing unit 860 is transmitted to the first ADF 891 and the second ADF 892. Accordingly, the first ADF 891 adaptively filters an output signal of the eleventh interface 862 based on a biosignal output from the differential amplifier 886, and the second ADF 892 adaptively filters an output signal of the twelfth interface 864 based on the biosignal output from the differential amplifier 886.

For example, the first ADF 891 adaptively filters the output signal of the eleventh interface 862 as the first switching device 868 is closed, based on a biosignal extracted by the differential amplifier 886, and the first adder 882 removes an output signal of the first ADF 891 from the output signal of the eleventh interface 862 as the first switching device 868 is opened. In addition, the second ADF 892 adaptively filters the output signal of the twelfth interface 864 as the first switching device 868 is closed, based on the biosignal extracted by the differential amplifier 886, and the second adder 884 removes an output signal of the second ADF 892 from the output signal of the twelfth interface 864 as the first switching device 868 is opened.

In accordance with the example illustrated in FIG. 8B, the differential amplifier 886 may perform differential amplification on an output signal of the first adder 882 and an output signal of the second adder 884, and output the biosignal. The first ADF 891 and the second ADF 892 of FIG. 8B are examples of the first ADF 388 and the second ADF 389 of FIG. 3B, and thus a repeated explanation thereof will not be given with respect to corresponding elements.

Figure 9:
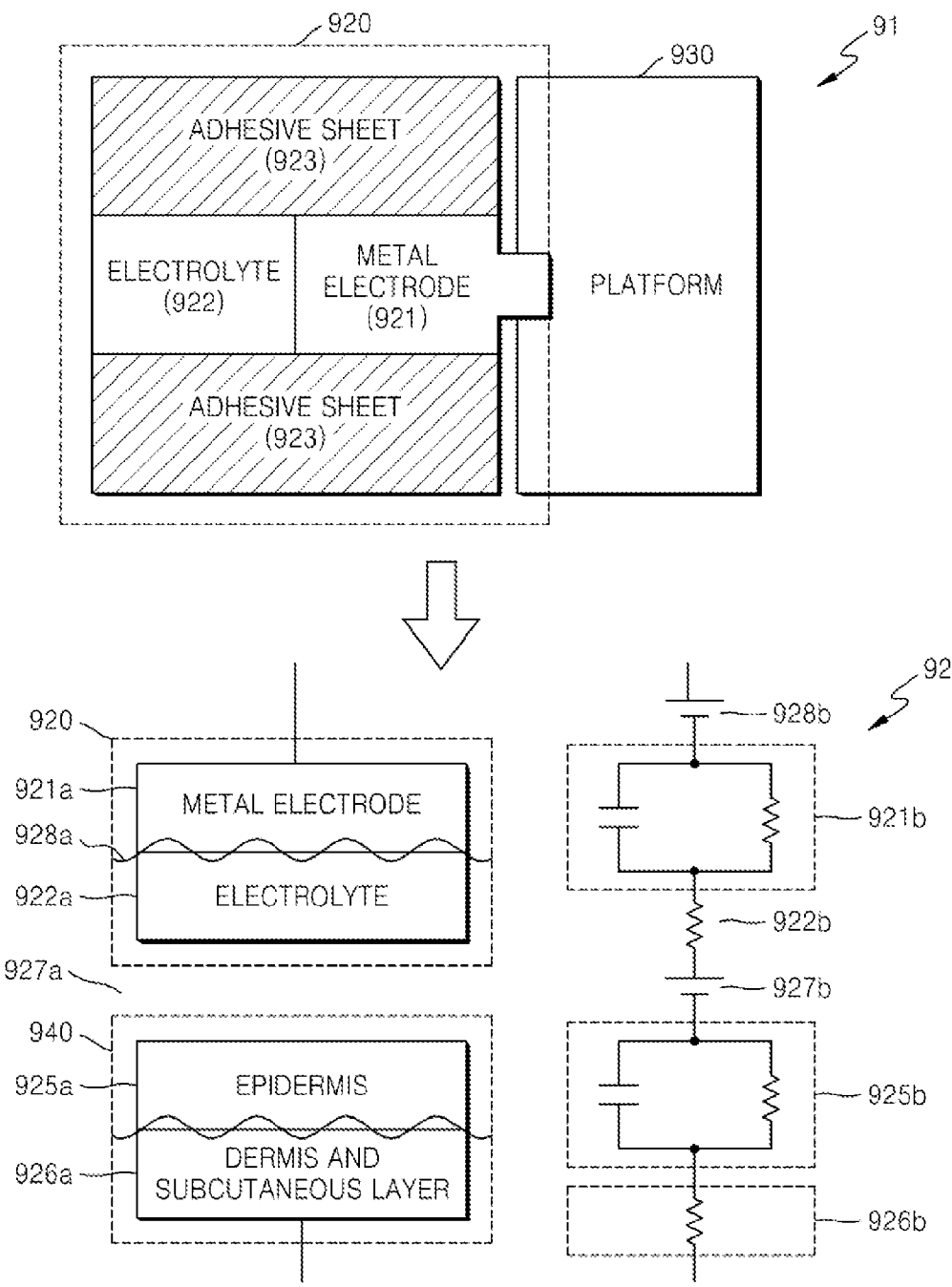
FIG. 9 is a block diagram illustrating an example of a structure of an interface and a circuit model corresponding to the interface.

FIG. 9 is a block diagram illustrating an example of a structure 91 of an interface 920 and a circuit model 92 corresponding to the interface 920. Referring to the example of the structure 91 of the interface 920 illustrated in FIG. 9, the interface 920 includes a metal electrode 921, an electrolyte 922, and an adhesive sheet 923. The metal electrode 921 electrically or mechanically connects the interface 920 and the apparatus 100, 200, 250, 300, 350, 500, 600, 700, 750, 800, or 850 via a platform 930. In an example of this case, the platform 930 is a sensing platform including a digital signal processor (DSP) or any other device known to one of ordinary skill in the art to connect the interface 920 and the apparatus 100, 200, 250, 300, 350, 500, 600, 700, 750, 800, or 850. In an example, the adhesive sheet 923 is attached to the skin of a subject, and the electrolyte 922 is a conductive gel.

Referring further to the example of the circuit model 92 corresponding to the interface 920 illustrated in FIG. 9, a metal electrode 921a corresponds to a capacitor and resistor component 921b, and an electrolyte 922a corresponds to a resistor component 922b. In addition, an epidermis 925a of the skin of the subject corresponds to a capacitor and resistor component 925b, and a dermis and subcutaneous layer 926a of the skin of the subject corresponds to a resistor component 926b.

In an additional example, a half cell potential is generated in double layers 927a and 928a where different materials contact each other, such as, for example, between the electrolyte 922 and a skin 940 of the subject, and between the metal electrode 921 and the electrolyte 922. In a further example, the double layers 927a and 928a correspond to power source components 927b and 928b.

As shown in the example illustrated in FIG. 9, a half cell potential is generated in the double layer where different materials contact each other, such as between the metal electrode 921 and the electrolyte 922 and between the electrolyte 922 and the skin 940 of the subject. Motion artifacts are generated as the electrical stability of such a double layer is broken due to the motion of the subject. Due to the motion artifacts, it is difficult to detect an accurate biosignal of the subject.

In accordance with the examples described herein, the apparatus 100, 200, 250, 300, 350, 500, 600, 700, 750, 800, or 850 may detect an accurate a noise signal by using the second interfacing unit 220, 270, 320, 370, 420, or 520 or by using the first switching device 618, 718, 778, 818, or 878 included in the interfacing unit 610, 710, 760, 810, 860, respectively, and thus, a biosignal with improved SNR characteristics may be detected.

Figure 10:
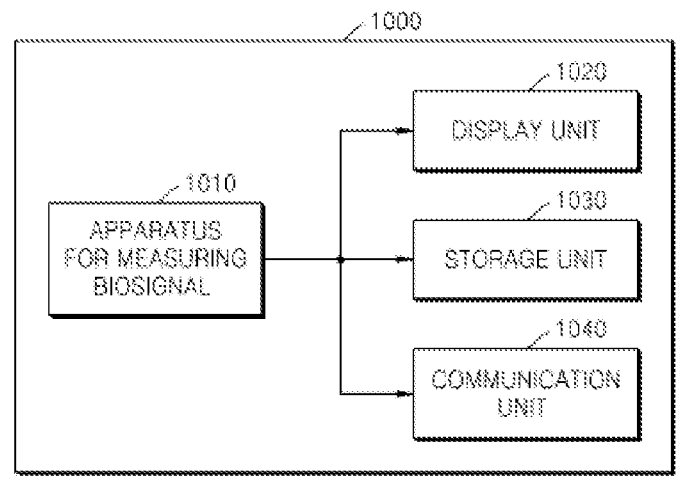
FIG. 10 is a block diagram illustrating an example of a medical imaging system.

FIG. 10 is a block diagram illustrating an example of a medical imaging system 1000. Referring to the example illustrated in FIG. 10, the medical imaging system 1000 includes a biosignal measuring apparatus 1010, a display unit 1020, a storage unit 1030, and a communication unit 1040.

Only elements included in the example of the medical imaging system 1000 illustrated in FIG. 10 are shown. Accordingly, one of ordinary skill in the art would understand that general-purpose elements other than the elements shown in FIG. 10 may be further included in the medical imaging system 1000.

The apparatus 1010 of FIG. 10 is at least one of the apparatuses 100, 200, 250, 300, 350, 500, 600, 700, 750, 800, or 850 of FIGS. 1 through 8B. Accordingly, the description with reference to FIGS. 1 through 8B may apply to the apparatus 1010 of FIG. 10, and thus, a repeated explanation will not be given with respect to corresponding elements.

The display unit 1020 displays a biosignal measured by the apparatus 1010. For example, examples of the display unit 1020 include a display panel, a liquid crystal display (LCD) screen, a monitor, and other output devices known to one of ordinary skill in the art, disposed on the medical imaging system 1000. However, it would be understood by one of ordinary skill in the art that the medical imaging system 1000 may not include the display unit 1020 and may include the communication unit 1040 configured to output a biosignal measured by the apparatus 1010 to an external display device (not shown).

The storage unit 1030 stores data generated while an operation of the medical imaging system 1000 is performed. It would be understood by one of ordinary skill in the art that examples of the storage unit 1030 may include a hard disc drive (HDD), a read-only memory (ROM), a random access memory (RAM), a flash memory, and a memory card.

In an example, the communication unit 1040 transmits and receives data to and from an external device through a wired or wireless network, or a wired serial communication network. For example, examples of the external device include another medical imaging system at a remote location, a general-purpose computer system, a personal digital assistant (PDA), a mobile terminal, and a facsimile. In an example of this case, while not being limited thereto, the network includes the Internet, a local area network (LAN), a wireless local area network (wireless LAN), a wide area network (WAN), a personal area network (PAN), and any network known to one of ordinary skill in the art to transmit and receive information. In a additional example, it would be understood by one of ordinary skill in the art that the storage unit 1300 and the communication unit 1400 further have image reading and searching functions and are integrated into a picture archiving communication system (PACS).

In accordance with the example illustrated in FIG. 10, the medical imaging system 1000 may display, store, or output a biosignal measured by the apparatus 1010 to an external device. Further, the utility of the biosignal measured by the apparatus 100, 200, 250, 300, 350, 500, 600, 700, 750, 800, or 850 may be improved.

Figure 11:
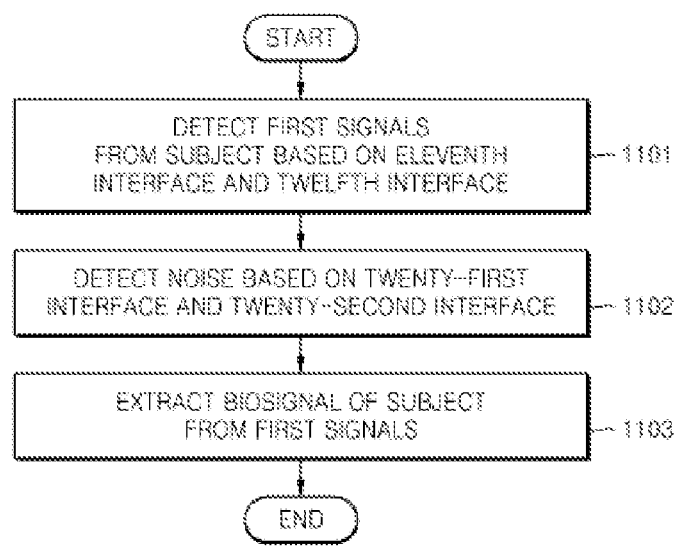
FIG. 11 is a flowchart illustrating an example of a method of measuring a biosignal.

FIG. 11 is a flowchart illustrating an example of a method of measuring a biosignal. Referring to the example illustrated in FIG. 11, the method may be performed by any of the apparatuses 100, 200, 250, 300, 350 of FIGS. 1 through 4 and the medical imaging system 1000 of FIG. 10. Accordingly, an omitted description which is related to the apparatuses 100, 200, 250, 300, and 350 of FIGS. 1 through 4 and the medical imaging system 1000 of FIG. 10 may apply to the method of FIG. 11.

First signals from a subject are detected (1101). For example, the first signals include a biosignal of the subject and noise. In an example, the first interfacing unit 110, 210, 260, 310, 360, and 410 respectively performs the detection using the eleventh interface 212, 262, 312, 362, and 412 and the twelfth interface 214, 264, 314, 364, and 414. Noise is detected (1102). In an example, the second interfacing unit 120, 220, 270, 320, 370, and 420 detects noise by using the twenty-first interface 222, 272, 322, 372, and 422 and the twenty-second interface 224, 274, 324, 374, and 424, which are connected to each other. In a further example, electrolytes included in the twenty-first interface 222, 272, 322, 372, and 422 and the twenty-second interface 224, 274, 324, 374, and 424 are connected to each other, and are hydrogels. In an alternative example, electrolytes included in the twenty-first interface 222, 272, 322, 372, and 422 and the twenty-second interface 224, 274, 324, 374, and 424 are connected to each other through a metal.

A biosignal is extracted (1103) from the first signals by using the detected noise. In an example, the biosignal extracting unit 130, 230, 280, 330, and 380 extracts a biosignal of the subject by using the detected first signals and the detected noise.

In accordance with the example illustrated in FIG. 11, the method may accurately detect the noise signal by using the twenty-first interface 222, 272, 322, 372, and 422 and the twenty-second interface 224, 274, 324, 374, and 424, which are connected to each other, and thus, a biosignal with improved SNR characteristics may be measured.

Figure 12:
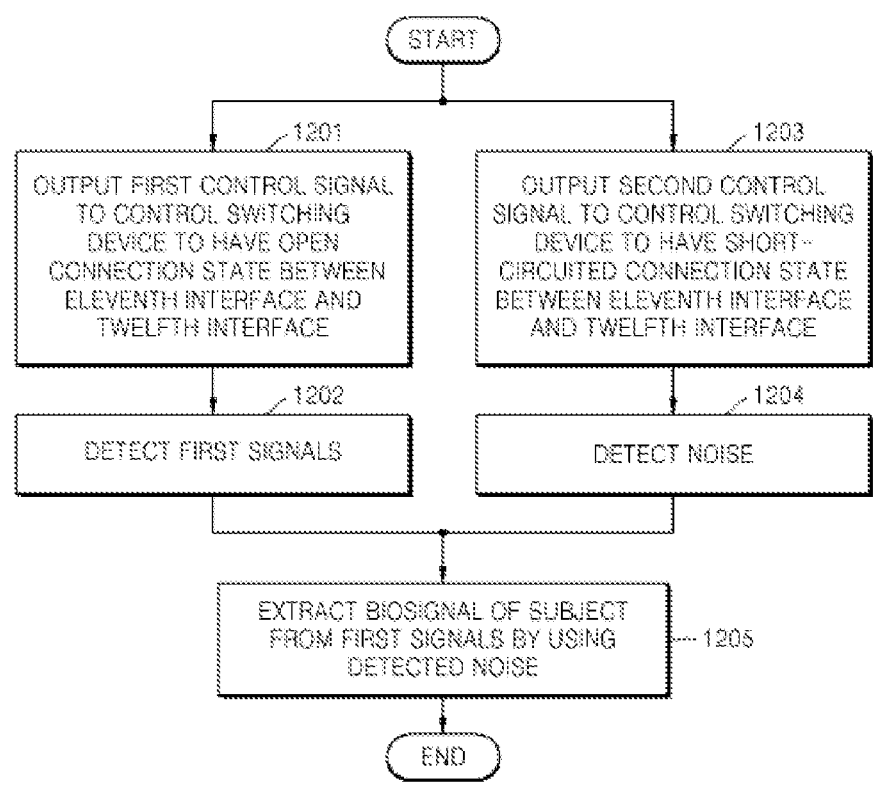
FIG. 12 is a flowchart illustrating another example of a method of measuring a biosignal.

FIG. 12 is a flowchart illustrating another example of a method of measuring a biosignal. Referring to the example illustrated in FIG. 12, the method may be performed by any of the apparatuses 600, 700, 750, 800, and 850 of FIGS. 6 through 8B and the medical imaging system 1000 of FIG. 10. Accordingly, an omitted description which is related to the apparatuses 600, 700, 750, 800, and 850 of FIGS. 6 through 8B and the medical imaging system 1000 of FIG. 10 may apply to the method of FIG. 12.

A first control signal, which is configured to control a first switching device 618, 718, 768, 818, and 868 to be a connection state that is opened between an eleventh interface 612, 712, 762, 812, and 862 and a twelfth interface 614, 714, 764, 814, and 864, is output (1201). In an example, the first control signal is output by a respective control unit 625, 725, 775, 825, and 875.

First signals are detected (1202) from a subject when the connection state between the eleventh interface 612, 712, 762, 812, and 862 and the twelfth interface 614, 714, 764, 814, and 864 is opened according to the outputted first control signal. In an example, the first signals are detected by the eleventh interface 612, 712, 762, 812, and 862 and the twelfth interface 614, 714, 764, 814, and 864. For example, the first signals include a biosignal of the subject and noise.

A second control signal, which is configured to control the first switching device 618, 718, 768, 818, and 868 to be a connection state that is short-circuited between the eleventh interface 612, 712, 762, 812, and 862 and the twelfth interface 614, 714, 764, 814, and 864, is output (1203). In an example, the second control signal is output by the respective control unit 625, 725, 775, 825, and 875.

Noise is detected (1204) as the connection state between the eleventh interface 612, 712, 762, 812, and 862 and the twelfth interface 614, 714, 764, 814, and 864 is short-circuited according to the outputted second control signal. In an example, the noise is detected by the eleventh interface 612, 712, 762, 812, and 862 and the twelfth interface 614, 714, 764, 814, and 864.

A biosignal of the subject is extracted (1205) from the detected first signals by using the detected noise. In an example, a biosignal extracting unit 630, 730, 780, 830, and 880 extracts the biosignal of the subject.

In accordance with the example illustrated in FIG. 12, the method may accurately detect the noise signal by using a switching device configured to switch a connection state between the interfaces, and, thus, a biosignal with improved SNR characteristics may be measured.

In an example of this case, various portions of the method may be changed. For example, the detection of the biosignal including noise and the noise signal may be performed prior to the respective output of the opening control signal and the short-circuiting control signal.

The units described herein may be implemented using hardware components, such as, for example, a processing device, and software components. A processing device may be implemented using one or more general-purpose or special purpose computers, such as, for example, a processor, an array of logic gates, a controller and an arithmetic logic unit, a digital signal processor, a microcomputer, a field programmable array, a programmable logic unit, a microprocessor, a combination of a general-purpose microprocessor and a memory in which a program executable in the general-purpose microprocessor is stored, or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such as parallel processors. As used herein, a processing device configured to implement a function A includes a processor programmed to run specific software. In addition, a processing device configured to implement a function A, a function B, and a function C may include configurations, such as, for example, a processor configured to implement both functions A, B, and C, a first processor configured to implement function A, and a second processor configured to implement functions B and C, a first processor to implement function A, a second processor configured to implement function B, and a third processor configured to implement function C, a first processor configured to implement function A, and a second processor configured to implement functions B and C, a first processor configured to implement functions A, B, C, and a second processor configured to implement functions A, B, and C, and so on.

The software components may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. For example, the software and data may be stored by computer readable recording media. Computer readable recording media may include any data storage device that can store data which can be thereafter read by a computer system or processing device. Examples of computer readable recording media include read-only memory (ROM), random-access memory (RAM), CD-ROMs, magnetic tapes, floppy disks, optical data storage devices.

Program instructions to perform a method described herein, or one or more operations thereof, may be recorded, stored, or fixed in computer-readable storage media. The program instructions may be implemented by a computer. For example, the computer may cause a processor to execute the program instructions. The media may include, alone or in combination with the program instructions, data files, data structures, and the like. Examples of computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as that which is produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable storage mediums. In addition, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. Further, described units to perform an operation or a method may be hardware, software, or some combination of hardware and software. For example, units may be a software package running on a computer or the computer on which that software is running.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A biosignal measuring apparatus, comprising:
   a first interfacing unit comprising two or more first interfaces configured to detect first signals, which comprises a biosignal and a noise signal, from a subject;
   a second interfacing unit comprising two or more second interfaces and a connecter, the second interfaces being configured to detect the noise signal from the subject, the connecter being configured to electrically connect the two or more second interfaces; and
   a biosignal extractor comprising:
      a first differential amplifier configured to perform differential amplification on the first signals to output a first result, and
      a second differential amplifier configured to perform differential amplification on the noise signal from the second interfaces unit to output a second result,
   wherein the biosignal extractor is configured to extract the biosignal of the subject by removing the second result from the first result.

2. The apparatus of claim 1, wherein the connecter is further configured to short-circuit the second interfaces.

3. The apparatus of claim 1, wherein the second interfaces comprise electrolytes, and
wherein the connecter comprises an electrolyte configured to connect the electrolytes of the second interfaces.

4. The apparatus of claim 3, wherein the electrolytes are hydrogels.

5. The apparatus of claim 1, wherein the second interfaces comprise electrolytes, and
wherein the connecter comprises a metal configured to connect the electrolytes of the second interfaces.

6. The apparatus of claim 5, wherein the electrolytes are hydrogels.

7. The apparatus of claim 1, wherein the first interfacing unit and the second interfacing unit are attached to a pad.

8. A biosignal measuring apparatus, comprising:
a first interfacing unit comprising two or more first interfaces configured to detect first signals, which comprises a biosignal and a noise signal, from a subject;
a second interfacing unit comprising two or more second interfaces and a connecter, the second interfaces being configured to detect the noise signal from the subject, the connecter being configured to electrically connect the two or more second interfaces; and
a biosignal extractor comprising:
a first differential amplifier configured to perform differential amplification on the first signals,
a second differential amplifier configured to perform differential amplification on the signals output from the second interfacing unit,
an adaptive filter configured to adaptively filter a signal output from the second differential amplifier based on a feedback from an adder, and
the adder is configured to remove the adaptively filtered signal from a signal output from the first differential amplifier.

9. A biosignal measuring apparatus, comprising:
a first interfacing unit comprising two or more first interfaces configured to detect first signals, which comprises a biosignal and a noise signal, from a subject;
a second interfacing unit comprising two or more second interfaces configured to detect the noise signal from the subject, a distance between the second interfaces being less than a distance between the first interfaces; and
a biosignal extractor comprising:
a first differential amplifier configured to perform differential amplification on the first signals to output a first result, and
a second differential amplifier configured to perform differential amplification on the noise signal from the second interfaces unit to output a second result,
wherein the biosignal extractor is configured to extract the biosignal of the subject by removing the second result from the first result.

10. The apparatus of claim 9, wherein the first interfacing unit and the second interfacing unit are attached to a pad.

11. A method of measuring a biosignal, the method comprising:
detecting first signals, which comprises a biosignal and a noise signal, from a subject based on an eleventh interface and a twelfth interface;
detecting the noise signal from the subject based on a twenty-first interface and a twenty-second interface connected to the twenty-first interface;
performing first differential amplification on the first signals, the first differential amplification outputting a first result;
performing second differential amplification on the noise signal output from the twenty-first interface and the twenty-second interface, the second differential amplification outputting a second result; and
extracting the biosignal of the subject from the first signals by removing the second result from the first result.

12. The apparatus of claim 8, wherein the adaptive filter is further configured to update a filter coefficient based on an artifact reduction percentage (ARP), a noise reduction ratio, and an SNR of the extracted biosignal.

* * * * *